United States Patent [19]

Allen et al.

[11] 4,438,119
[45] Mar. 20, 1984

[54] METHOD FOR ALLEVIATION OF EXTRAPYRAMIDAL MOTOR DISORDERS

[75] Inventors: Lloyd E. Allen, Evansville; Leslie A. Riblet, Mt. Vernon, both of Ind.

[73] Assignee: Mead Johnson & Company, Evansville, Ind.

[21] Appl. No.: 452,686

[22] Filed: Dec. 23, 1982

[51] Int. Cl.³ ............................................ A61K 31/505
[52] U.S. Cl. ................................................... 424/251
[58] Field of Search ......................................... 424/251

[56] References Cited

U.S. PATENT DOCUMENTS

| | | | |
|---|---|---|---|
| 3,717,634 | 2/1973 | Wu et al. | 424/251 |
| 3,976,776 | 8/1976 | Wu et al. | 424/251 |
| 4,182,763 | 1/1980 | Casten et al. | 424/251 |

OTHER PUBLICATIONS

Merck Manual, 14th Ed., pp. 1357-1364, (1982).

Sovner et al., "Psychopharmacology: A Generation of Progress", Raven Press, N.Y., 1021-1032, (1978).
Marsden et al., "Psychiatric Aspects of Neurological Disease", Grune & Stratton, N.Y., (1975), pp. 291-265.
Y. H. Wu et al., *J. Med. Chem.*, 15, 477, (1972).
G. L. Sathananthan et al., Current Therapeutic Research, 701-705, (1975).
Allen et al., Arzneim. Forsch., 24, No. 6, 917-922, (1974).

*Primary Examiner*—Stanley J. Friedman
*Attorney, Agent, or Firm*—Richard P. Ryan; Robert H. Uloth

[57] ABSTRACT

Buspirone and its pharmaceutically acceptable salts are useful in alleviation of extrapyramidal motor disorders which can take the form of clinical syndromes such as Parkinsonism and neuroleptic-induced extrapyramidal symptoms (EPS).

8 Claims, No Drawings

METHOD FOR ALLEVIATION OF EXTRAPYRAMIDAL MOTOR DISORDERS

FIELD OF THE INVENTION

This invention is concerned with a drug bio-affecting and body-treating process which employs the pyrimidine compound 8-[4-[4-(2-pyrimidinyl)-1-piperazinyl]-butyl]-8-azaspiro[4.5]decane-7,9-dione or a pharmaceutical acceptable acid addition salt thereof (Class 424, Subclass 251).

BACKGROUND OF THE INVENTION

The pyrimidine compound with which the present invention is concerned has the following structural formula

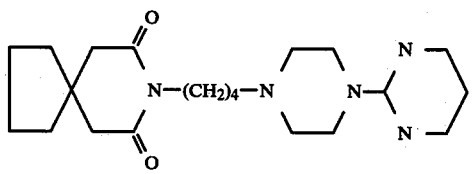

and is known as buspirone. The hydrochloride salt has been referred to in the prior art as MJ 9022-1 and as buspirone hydrochloride. Other acid addition salts thereof are named by combining "buspirone" with the appropriate word to define the acid from which it is prepared as in "buspirone hydrochloride." The latter is the United States Adopted Name (USAN); refer to *J. American Med. Assoc.* 225, 520 (1973).

The synthesis of the compound and the disclosure of its psychotropic properties are described in the following patents and publications.

1. Y. H. Wu, et al., *J. Med. Chem.*, 15, 477 (1972).
2. Y. H. Wu, et al., U.S. Pat. No. 3,717,634 patented Feb. 20, 1973.
3. L. E. Allen, et al., *Arzneium. Forsch.*, 24, No. 6, 917-922 (1974).
4. G. L. Sathananthan, et al., *Current Therapeutic Research*, 18/5, 701-705 (1975).
5. Y. H. Wu, et al., U.S. Pat. No. 3,976,776, patented Aug. 24, 1976.

The use of buspirone hydrochloride as an anti-anxiety agent for the treatment of neurotic patients is described in G. P. Casten, et al., U.S. Pat. No. 4,182,763 patented Jan. 8, 1980. Currently, clinical studies to support a submission to U.S. Food & Drug Administration for the use of buspirone in treatment of anxiety neurosis are being conducted.

The present invention can be distinguished from this prior art in that it involves a distinct patient population characterized by a disease state different from the anxiolytic process disclosed in the prior art.

The extrapyramidal system and its disorders are familiar to medical practitioners whose specialities are associated with neurological disorders as contrasted with psychiatric disorders addressed by buspirone prior art. For background, summaries of this area are available ranging from the very concise, e.g. cf: The Merck Manual, 14th Edition, Section 132, page 1357-1364 (1982) to detailed reviews such as Sovner and DiMascio, "Psychopharmacology: A Generation of Progress", Lipton, DiMascio, and Killam (Eds.), Raven Press, N.Y., 1978, pp. 1021-1032; and Marsden, et al., "Psychiatric Aspects of Neurological Disease", Benson and Blumers (Eds.), Grune and Stratton, N.Y., 1975, pp. 219-265.

Essentially, extrapyramidal disorders can be characterized by symptoms such as involuntary movements (tremors, tics, etc.); impairment of voluntary movement (brady-, hypo-, or akinesia); and changes in muscle tone and posture (dystonia, muscle rigidity, dysequilibrium). Parkinsonism, neuroleptic-induced extrapyramidal symptoms (EPS), and tardive dyskinesia are examples of discrete extrapyramidal motor disorders. Such disorders may arise spontaneously or as a consequence of drug administration.

SUMMARY OF THE INVENTION

The process of the present invention is intended for the alleviation of extrapyramidal motor disorders of which Parkinsonism and drug-induced extrapyramidal symptoms (EPS) are two specific examples. The process essentially involves administration of buspirone, or a pharmaceutically acceptable acid addition salt thereof, to one in need of such treatment. Pharmaceutically acceptable acid addition salts of buspirone and methods of pharmaceutical formulation are described in the above patents of Wu, et al., U.S. Pat. No. 3,717,634 and Casten, et al., U.S. Pat. No. 4,182,763 which are incorporated herein in their entirety by reference. For use in the instant process oral administration of buspirone hydrochloride from about 10 mg to 60 mg in divided doses is anticipated as being the preferred dosage regimen.

DETAILED DESCRIPTION OF THE INVENTION

Catalepsy, resulting from central nervous system dysfunction, is observed to be a common clinical feature in neurological, psychological, and iatrogenic disorders including extrapyramidal disease, cationic schizophrenia and the cluster of neuroleptic-induced side effects collectively known as "extrapyramidal side-effects'-'(EPS). In man, catalepsy is manifested by akinesia, a state of indifference with loss of affect, frozen postures and hypomimia (mask-like face), while catalepsy in animals takes the form of akinesia and the prolonged maintenance of imposed, usually awkward postures.

In the cataleptic state animals retain muscle tone, react to painful stimuli and retain righting reflexes but they do not extricate themselves from awkward postures and are not spontaneously active. Drug-induced catalepsy in laboratory animals serves as a basis for pharmacologic testing. The degree of drug-induced catalepsy in laboratory animals can be assessed by: (a) prolonged retention of rats' forepaws over an elevated horizontal bar or on top of a platform, (b) clinging and remaining motionless on a vertical wire grid, while normal rats climb, (c) maintenance of awkward, imposed postures, and (d) impaired performance in an open field test in which neuroleptic-treated animals remain motionless while normal rats run rapidly to the walls.

Neuroleptic drugs given as antipsychotic agents, which clinically cause Parkinsonian symptoms in man, induce catalepsy when administered to animals. This neuroleptic-induced akinetic syndrome in animals has become an accepted model for clinical EPS in man. The usefulness of this animal model is strengthened by the generally good correlation between the cataleptic effects of neuroleptics in these animal studies and the incidence of EPS in man following their use. Those agents which fail to cause significant extrapyramidal effects in man also fail to induce catalepsy in experimental animals. As an extension, agents which demonstrate the ability to reverse this drug-induced catalepsy become candidates for alleviation of these disorders of the extrapyrimidal system. As an example, anticholinergic agents, a major class of drugs used clinically to treat extrapyramidal motor disorders, reverse this drug-induced catalepsy in the rat. Other drugs which have been used for treatment of extrapyramidal motor disorders represent a number of pharmacologic classes; e.g., anticholinergic agents (as mentioned above), antihistamines, dopamine-releasers such as adamantine, dopamine precursors, DOPA decarboxylase inhibitors, bromocryptine, and diazepam.

The instant invention relates from the observation that buspirone, a drug which is structurally unrelated to those presently used to treat extrapyramidal motor disorders, potently reverses phenothiazine-induced catalepsy in the rat. The mechanism of this action is uncertain but it has previously been shown that buspirone is free of anticholinergic activity. In keeping with its activity in the phenothiazine-induced cataleptic rat, buspirone may be expected to be useful in alleviating specific syndromes in man which are classified as extrapyramidal motor disorders. Administration of buspirone would be indicated for treatment of Parkinsonism, neuroleptic-induced extrapyramidal symptoms (EPS) and tardive dyskinesia. The usefulness of buspirone treatment in Parkinsonism and clincal EPS would be expected on the basis of the previous correlation between the laboratory animal test results and clincal applicability to these symptoms. Certain aspects of buspirone's pharmacology suggest that its administration might be useful in the treatment of tardive dyskinesia. Not only does buspirone produce a potent reversal of neuroleptic-induced catalepsy, but it also reverses catalepsy induced by dopamine-depleting agents which suggests that its anticataleptic actions are independent of its actions on the dopaminergic system. The relevance of these mechanistic considerations become more clear in light of the more detailed psychopharmacological reviews cited hereinabove in the Background of the Invention section.

Administration of buspirone according to the present invention may be by the parenteral, oral, or rectal routes. The oral route is preferred, however. Dosage levels of 4–10 mg/kg which have been effective in catalepsy reversal in animal testing are similar to the levels which elicit anxiolytic effects. The clinical dosage range for alleviation of extrapyramidal motor disorders is about the same as for anti-anxiety usage, but may vary to some extent with the amount of buspirone administered being less than about 100 mg per day, generally in the 10 mg to 60 mg range, and preferably in the range of 20–30 mg per day. Since the dosage should be tailored to the individual patient, a usual practice is to commence with a dose of about 5 mg administered two or three times per day and then to increase the dose every two or three days by 5 mg at each dosage time until the desired response is observed or until the patient exhibits side effects. Single daily dosage may be applicable in some instances.

DESCRIPTION OF SPECIFIC EMBODIMENTS

EXAMPLE 1

Phenothiazine-Induced Catalepsy Model

Fasted, male rats were divided into groups of 10 each and dosed with trifluoperazine (15 mg/kg, orally). The animals were then placed in individual cages located in a quiet room. At time intervals of 1 and 2 hours the animals were checked for catalepsy by carefully picking them up and placing their front feet on the top edge of the cage side. If the animal remained motionless in this position for 30 seconds, catalepsy was considered to be present. At $2\frac{1}{2}$ hours following trifluoperazine dosing, the test compound was administered orally in varying dose levels. Thirty minutes after administration of the test compound (3 hours post trifluoperazine administration), the animals were checked for catalepsy reversal. Normally, at this time interval, the trifluoperazine would produce catalepsy in 100% of the animals. $ED_{50}$ (95% fiducial limits) values were determined according to the method of Berkson (J. Berkson, *J. American Statistical Association*, 48:565–599 (1953)).

The following results were obtained for buspirone hydrochloride.

| Dose mg/kg (p.o.) | No. reversed No. tested | % Reversed |
|---|---|---|
| 10 | 10/10 | 100 |
| 5 | 8/10 | 80 |
| 2.5 | 2/10 | 20 |

These results gave an $ED_{50}$ value of 3.6 (2.6–4.9) mg/kg for buspirone hydrochloride.

What is claimed is:

1. A method for alleviation of extrapyramidal motor disorders which comprises administering a non-toxic therapeutically effective dose of buspirone or a pharmaceutically acceptable acid addition salt thereof to a mammal in need of such treatment.

2. The method of claim 1 wherein buspirone hydrochloride is employed, and dosage is by the oral route.

3. The method of claim 1 wherein Parkinsonism is the specific extrapyramidal motor disorder afflicting said mammal.

4. The method of claim 1 wherein neuroleptic-induced extrapyramidal symptoms (EPS) is the specific extrapyramidal disorder afflicting said mammal.

5. The method of claim 1 wherein tardive dyskinesia is the specific extrapyramidal disorder afflicting said mammal.

6. The method of claims 2, 3, or 4 wherein said mammal is an adult and a daily dose of from about 10 mg to 60 mg is employed.

7. The method of claim 6 wherein said daily dose is divided and administered b.i.d.

8. the method of claim 6 wherein said daily dose is divided and administered t.i.d.

* * * * *